United States Patent

Weiss et al.

[11] Patent Number: 5,036,839
[45] Date of Patent: Aug. 6, 1991

[54] SUPPORTER

[76] Inventors: Arieh Weiss, 1217 Normandy Dr., Apt. 8, Miami Beach, Fla. 33141; Raymond M. Weiss, 19 Pratt Ave., Apt. 3N, Mt. Vernon, N.Y. 10550

[21] Appl. No.: 502,749

[22] Filed: Apr. 2, 1990

[51] Int. Cl.$^5$ ............................................. A61F 5/40
[52] U.S. Cl. .................................... 128/162; 128/158
[58] Field of Search .......................... 128/79, 158-162, 128/168, 171, 96.1, 845, 849

[56] References Cited

U.S. PATENT DOCUMENTS

| | | | |
|---|---|---|---|
| 3,225,761 | 12/1965 | Swensen | 128/158 |
| 3,518,995 | 7/1970 | Claff | 128/158 X |
| 4,059,103 | 11/1977 | Glaser | 128/96.1 |
| 4,378,010 | 3/1983 | McDonald | 128/168 |
| 4,590,931 | 5/1986 | Kidwell, Jr. | 128/162 |

Primary Examiner—Robert A. Hafer
Assistant Examiner—Kerry Owens
Attorney, Agent, or Firm—Alvin S. Blum

[57] ABSTRACT

A supporter encloses the scrotum in a porous pouch having a top opening. The top opening of the pouch is drawn closed with a closure about the tissue at the top of the scrotum and penis. This is the point of smallest diameter. When closed, the pouch is held in place at the closure without need for straps around the body and without undue tightness at the closure. The embodiment for support of the scrotum has an aperture for the penis to pass through. In an alternative embodiment for urinary incontinence, the pouch encloses both penis and scrotum. It is lined with absorbent material and has a waterproof outer coating.

17 Claims, 1 Drawing Sheet

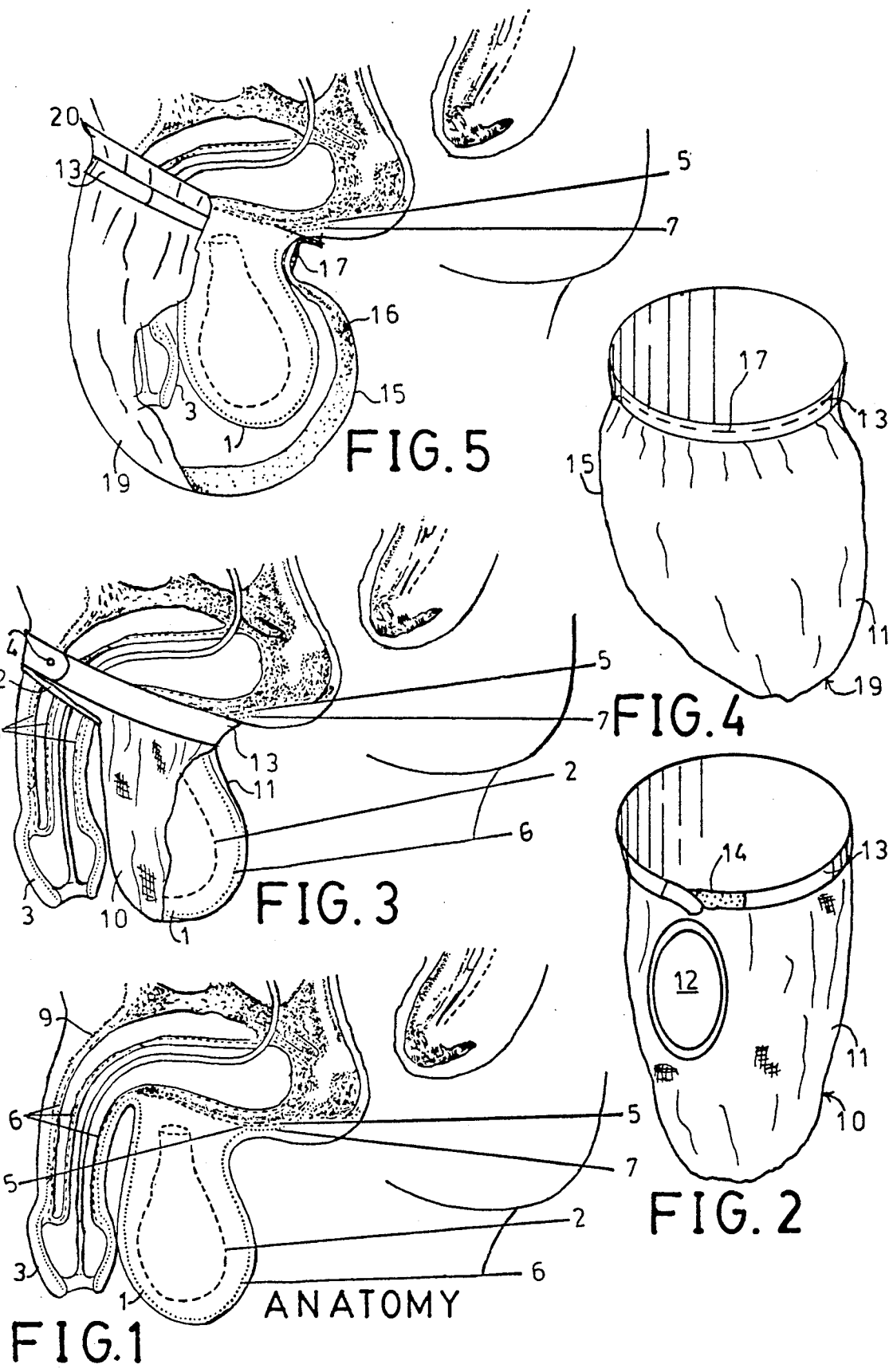

SUPPORTER

This invention relates to enclosures and supporters for body parts and more particularly to enclosures and supporters for the scrotum and the penis of humans.

BACKGROUND OF THE INVENTION

The testes in humans must be maintained at a temperature below that of the rest of the body in order for sperm to mature. In fetal life they migrate out of the body cavity, through the inguinal canal to the scotal sac. When cold, the scrotal surface contracts in corrugations, supporting the testes close to the body. When warm, and in illness and the aged, the scrotum relaxes and the testes may hang uncomfortably low. Supporters that support the scrotum may also support the penis in some models. These generally employ straps that encircle the body and that may also pass between the legs to hold up the supporter. This construction is also characteristic of waterproof enclosures for male incontinence of urine. These multiple straps are awkward and uncomfortable to put in place and to wear.

SUMMARY OF THE INVENTION

It is accordingly an object of the invention to provide a supporter that encloses the scrotum or that encloses the scrotum and the penis of humans that is effectively held in place without straps that encircle the body or the legs.

It is another object of the invention that the supporter by easy to apply and confortable to wear.

The invention comprises a pouch for the scrotum that may also enclose the penis in an alternative embodiment. The pouch has a top opening that is large enough to pass the scrotum and that is arranged to encircle and draw closed about the tissue above the junction of the scrotum and the root of the penis. This is a point of smallest diameter. When the top opening is closed down to this size, the pouch cannot slide down and it is thus supported without the use of straps and without having to close the opening so tightly as to be uncomfortable. The embodiment for incontinence encloses the penis as well and is lined with absorbent material with a waterfroof shell and may be disposable.

These and other objects, advantages and features of the invention will become more apparent when the detailed description is read in conjunction with the drawings.

BRIEF DESCRIPTION OF THE DRAWINGS

FIG. 1 shows normal male genital anatomy in cross section.

FIG. 2 shows the scrotal supporter of the invention in perspective view.

FIG. 3 shows the supporter of FIG. 2 in position on the body with a portion broken away partially in cross section.

FIG. 4 shows another embodiment of the invention for urinary incontinence in perspective view.

FIG. 5 shows the embodiment of FIG. 4 in position on the body with a portion broken away partially in cross section.

DETAILED DESCRIPTION OF THE PREFERRED EMBODIMENTS

Referring now first to FIG. 1, the normal male genital anatomy is shown. The external spermatic fascia 2 encloses the testes. Another fascia layer, the tunica dartos 6 containing connective tissue and muscle lies just beneath the skin of the scrotum 1. This tunica dartos layer also encloses the penis 3 and extends to the root of the penis 9 anteriorly and is connected posteriorly to the superficial perineal fascia 5. Consequently, there is, at the junction of the root of penis and scrotum with the torso, a strong support structure. It is at this site that the supporters of the invention are secured by an encircling band.

FIGS. 2 and 3 show a scrotal supporter 10 of the invention. It consists of a porous fabric pouch 11 having an aperture 12 through which the penis 3 passes so that the pouch only supports the scrotum 1. At the top of the pouch a band or hem 13 has a closure 14 that is adjustable so as to snugly encircle the tissue at this location at the base of the penis and scrotum. Becuase this is the point of smallest diameter, the pouch and its contents are held up securely without requiring the band to be applied so tightly as to be uncomfortable or to constrict circulation. In practice the device is so easily held in place that the user is unaware of its presence after a few minutes. The aforementioned fascial layers are not stressed because they normally carry this load except for the extra weight of the pouch 11 which is insignificant.

The closure may be any one of the closures well known in the garment arts, including drawstrings, snaps, buttons, hook and loop, fasteners, elastics and the like. The hook and loop fastener has been found useful because it is easily adjusted and applied.

The embodiment 19 shown in FIG. 4 and 5 has a pouch 11 that encloses both penis and scrotum. It has a waterproof outer shell 15 and an absorbent inner liner 16. The band or hem 13 has a closure that is preferably an encircling elastic band 17. There may be an absorbent portion 20 above the closure 14. This embodiment is to catch and retain small amounts of urine without wetting the clothes. It is preferably made out of absorbent paper with a waterproof outer surface treatment and may be disposable. It may be changed without undressing and with a minimum of effort so that the wearer can lead a more normal life.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

We claim:

1. A pouch for enclosing the male genitalia comprising;
    a) a single sheet of material forming a resilient chamber;
    b) a top opening in said chamber having dimensions great enough to permit passage of the penis and scrotum therethrough;
    c) a closure means encircling said top opening for securing said pouch above the penis and scrotum at the point of smallest diameter, wherein said pouch is pulled upward and is secured in position without constricting the user; and d) a fastener means for removably holding said closure in a closed position.

2. The pouch according to claim 1 for supporting the scrotum including an aperture in the wall of said chamber, said aperture arranged to pass the penis therethrough so that the penis is free of said chamber.

3. The pouch according to claim 1 formed of a porous fabric.

4. The pouch according to claim 1, in which said fastener means is a drawstring.

5. The pouch according to claim 1, in which said fastener means is an elastic band.

6. The pouch according to claim 1, in which said fastener means is a hook and loop fastener.

7. The pouch according to claim 1, in which said fastener means is a snap fastener.

8. The pouch according to claim 1, in which said fastener means is a button fastener.

9. The pouch according to claim 1 for use with urinary incontinence in which said chamber is lined with moisture absorbent material.

10. The pouch according to claim 9, in which said chamber has a water resistant exterior surface.

11. A pouch for enclosing the male genitalia comprising;
   a) a single sheet of material forming a resilient chamber;
   b) a top opening in said chamber having dimensions great enough to permit passage of the penis and scrotum therethrough;
   c) a closure means encircling said top opening for securing said pouch above the penis and scrotum at the point of smallest diameter, wherein said pouch is pulled upward and is secured in position without constricting the user;
   d) a passage means in said single sheet for passing the penis therethrough, said passage means comprising an oval aperture; and
   e) a fastener means for removably holding said closure in a closed position.

12. The supporter of claim 11, in which said closure means is a band of fabric attached to said pouch at said top opening.

13. The supporter of claim 12, in which said fastening means is of the hook and loop type.

14. The supporter of claim 12, in which said fastening means is an elastic band.

15. The supporter of claim 12, in which said fastening means is a drawstring.

16. The supporter of claim 12, in which said fastening means is a snap fastener.

17. The supporter of claim 12, in which said fastening means is a button fastener.

* * * * *